United States Patent
Seino et al.

(10) Patent No.: US 7,217,352 B2
(45) Date of Patent: May 15, 2007

(54) CAPILLARY ELECTROPHORESIS DEVICE

(75) Inventors: Taisaku Seino, Hitachinaka (JP);
Tomoyuki Sakai, Kokubunji (JP);
Miho Ozawa, Abiko (JP); Masaya Kojima, Mito (JP); Eric S. Nordman, Foster City, CA (US)

(73) Assignees: Hitachi High-Technologies Corporation, Tokyo (JP); Applera Corporation, Foster City, CA (US)

( * ) Notice: Subject to any disclaimer, the term of this patent is extended or adjusted under 35 U.S.C. 154(b) by 359 days.

(21) Appl. No.: 10/446,107

(22) Filed: May 28, 2003

(65) Prior Publication Data

US 2003/0221965 A1 Dec. 4, 2003

(30) Foreign Application Priority Data

May 31, 2002 (JP) ............................. 2002-159157

(51) Int. Cl.
*G01N 27/26* (2006.01)
(52) U.S. Cl. ................. 204/603; 204/605; 204/608; 204/612; 422/63; 422/99; 422/100; 422/101
(58) Field of Classification Search ................ 204/603, 204/605, 608, 612; 422/63, 99, 100, 101
See application file for complete search history.

(56) References Cited

U.S. PATENT DOCUMENTS

| | | | |
|---|---|---|---|
| 3,952,521 A | 4/1976 | Potter | |
| 4,912,789 A | 4/1990 | Maxwell | |
| 5,370,258 A | 12/1994 | Fair | |
| 5,887,616 A * | 3/1999 | Ikeda et al. | 137/558 |
| 6,132,685 A | 10/2000 | Kercso et al. | |
| 6,241,949 B1 * | 6/2001 | Kane | 422/102 |
| 6,375,819 B1 * | 4/2002 | Li et al. | 204/455 |
| 2002/0009392 A1 | 1/2002 | Wolk et al. | |

FOREIGN PATENT DOCUMENTS

WO   WO 01/89697 A2 * 11/2001

* cited by examiner

*Primary Examiner*—Nam Nguyen
*Assistant Examiner*—Anthony Fick
(74) *Attorney, Agent, or Firm*—Dickstein Shapiro LLP

(57) ABSTRACT

An electrophoresis device is disclosed that is capable of reducing waves occurring in a fluid in which the capillary tips of a capillary assay are immersed. A plurality of partition plate members can be provided in a container containing the fluid to divide the surface of the fluid into several sections. The container can be transported at a high speed, and the capillary tips can be immersed in the fluid quickly, thereby preventing resolution degradation caused by a long period of exposure of the capillary tips to air. Throughput of sample analysis can also be improved because it is not necessary to wait until waves disappear before conducting an analysis.

22 Claims, 16 Drawing Sheets

Fig.11 (b)

Operating process of assay

| Order | Operation Mode | Objective container | Container position before transfer → Destination |
|---|---|---|---|
| 1 | Container transfer | Waste-liquid container | Waste-liquid container holder → Array position |
| 2 | Gel filling | | |
| 3 | Container transfer | Waste-liquid container | Array position → Waste-liquid container holder |
| 4 | Container transfer | Washing water container | Washing water container holder section → Array position |
| 5 | Array washing | | |
| 6 | Container transfer | Washing water container | Array position → Washing water container holder section |
| 7 | Container transfer | Buffer container | Buffer container holder section → Array position |
| 8 | Pre-electrophoresis | | |
| 9 | Container transfer | Buffer container | Array position → Buffer container holder section |
| 10 | Container transfer | Washing water container | Washing water container holder section → Array position |
| 11 | Array washing | | |
| 12 | Container transfer | Washing water container | Array position → Washing water container holder section |
| 13 | Container transfer | Sample container | Parking area → Array position |
| 14 | Sample injection | | |
| 15 | Container transfer | Sample container | Array position → Parking area |
| 16 | Container transfer | Washing water container | Washing water container holder section → Array position |
| 17 | Array washing | | |
| 18 | Container transfer | Washing water container | Array position → Washing water container holder section |
| 19 | Container transfer | Buffer container | Buffer container holder section → Array position |
| 20 | Electrophoresis | | |
| 21 | Container transfer | Buffer container | Array position → Buffer container holder section |
| 22 | Container transfer | Sample container | Parking area → Receiver |
| 23 | Container transfer | Buffer container | Buffer container holder section → Array position |

CAPILLARY ELECTROPHORESIS DEVICE

FIELD

The present teachings relate to a capillary electrophoresis device for separating and analyzing samples, such as nucleic aids and proteins.

BACKGROUND

An example of a known device includes the Genetic Analyzer 3100, manufactured by Applied Biosystems. This analyzer can contain a buffer and a washing solution in a generally rectangular parallelepiped container having a smooth inner face. The analyzer can have a sample container, a buffer container, a washing solution container, and a waste liquid container on the same platform. Analyses can be carried out by moving the platform.

SUMMARY

The present teachings relate to achieving resolution and throughput improvements in a capillary electrophoresis device.

The present teachings relate to an electrophoresis device capable of reducing waves generated in a fluid in which capillary tips are immersed. A container holding the fluid can be provided and can include a plurality of partition plate members that can divide the fluid surface into several sections. Because the container holding the fluid can be transported at a high speed, the capillary tips can be immersed in the fluid quickly, thereby shortening the period of time that the capillary tips are exposed to air. This can prevent resolution degradation caused by exposure of the capillary tips to air. It is unnecessary to postpone the assay until the waves disappear, thereby improving throughput of sample analysis.

The present teachings relate to an electrophoresis device having a capillary tip exposure period of a predetermined duration. For example, the air exposure period of the capillary tip, from pre-electrophoresis to sample injection, can be 14 seconds or less. As a result, resolution degradation can be substantially prevented.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description herein and appended claims.

It is to be understood that both the foregoing general description and the following detailed description are exemplary and explanatory only, and are intended to provide an explanation of various embodiments of the present teachings.

DESCRIPTION OF THE VARIOUS EMBODIMENTS

Figure 1:
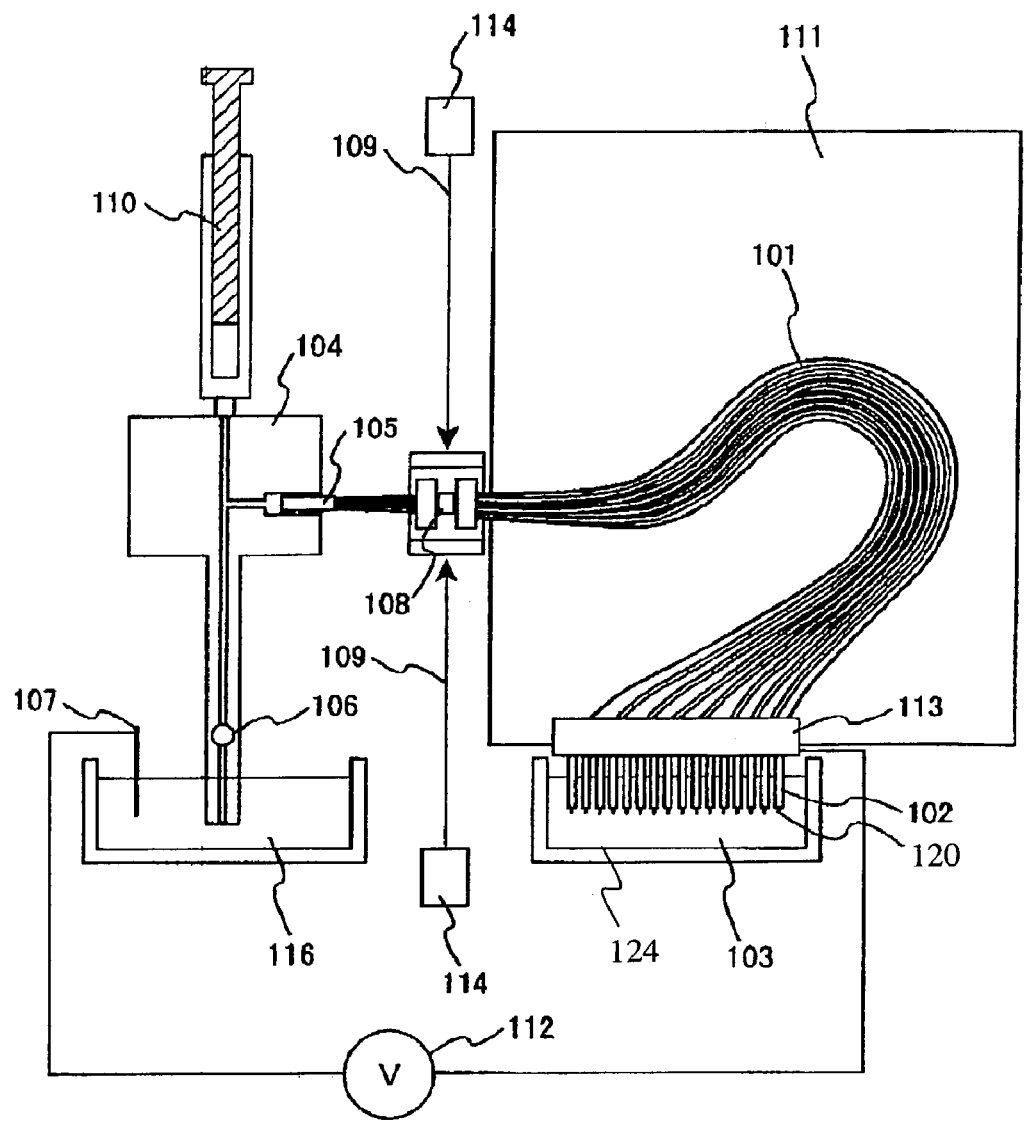
FIG. 1 is a schematic view showing an electrophoresis device according to various embodiments.

FIG. 1 is a schematic view of a capillary electrophoresis device according to various embodiments. The device can include a capillary array, a sample container, a buffer container, a separation medium replenishment system, an optical system, a power source system, and a thermostatic oven.

According to various embodiments, the capillary array can be a replaceable member including 96 capillaries 101. The capillary array can include a load header 113, a detection cell 108, and a capillary head 105. During use, the quality of the capillaries 101 can deteriorate after about 100 assays. As a result, it can be beneficial to replace the capillary array after about 100 assays to maintain the quality of the capillaries 101 and the performance of the device.

According to various embodiments, the capillaries 101 can be hollow members, and can be used for electrophoretic separation of samples. For example, the capillaries 101 can be formed of fused silica, and can have an outer diameter of about 0.15 mm, and an inner diameter of about 0.05 mm. The outer surface of the capillaries 101 can be coated with a polyimide resin, for example. However, the coating can be removed or not applied at a portion of the capillaries 101 that can be illuminated with a laser light. A separation medium and a buffer as a medium for electrophoresis, can be injected into the capillaries 101. Sample injection can be conducted by electrophoresis while immersing one end of the capillaries 101, for example the injecting end portions 120, into the sample 103. Electrophoresis separation after sample injection can be further performed while immersing the injecting end portions 120 into a buffer.

According to various embodiments, the load header 113 is a member that can be used to hold the injecting end portions 120 of the capillaries 101 at a predetermined position when applying a high voltage. For example, the load header 113 can hold hollow electrodes 102 (micro-sized stainless steel tubes) in an 8×12 matrix arrangement. The capillaries 101 can pass through the inside of each hollow electrode 102 and can be fixed so that the injecting end portions 120 slightly project and can be exposed. This can enable the precise arrangement of 96 injecting end portions 120, thereby reliably immersing them in the sample 103 held in the sample container. A high voltage can be applied to the hollow electrodes 102, whereby each hollow electrode 102 can form one end of a current-carrying path during electrophoresis.

According to various embodiments, the detection cell 108 can be a component capable of enabling the acquisition of information from the sample 103. When the detection cell 108 is illuminated with excitation light, it can emit light having wavelengths corresponding to the components of the sample being analyzed in the capillaries 101. The 96 capillaries 101 can be arranged and fixed on an optically flat surface as a standard base with a height tolerance of a few microns. During electrophoresis, two substantially coaxial beams of laser light 109 can be received on sides of the detection cell 108, so that light can be continuously transmitted through all of the light illuminated portions of the capillaries 101. The laser light 109 can cause the sample in the capillaries 101 to emit light (fluorescence having sample-dependent wavelengths) via the light-illumination portions of the capillaries 101. The emitted light can be detected by a light receiving optical system and can be used to analyze the sample.

According to various embodiments, a capillary head 105 can be a component that is capable of attaching and detaching filling end portions of the capillaries 101 (arranged opposite to the injecting end portions 120) to a separation medium block 104 in a pressure-tight and sealed manner. The capillary head 105 can bundle the 96 filling end portions of the capillaries 101 together in a group, and can provide a pressure-tight sealed connection to the separation medium block 104. The capillaries 101 can then be filled with a new separation medium through the filling end portions by high pressure from a syringe 110. A waste solution container can be placed in the vicinity of the injecting end portions 120 of the capillaries 101 to collect separation medium discharged from the injecting end portions 120.

According to various embodiments, a sample container 124 can have sample vessels each filled with several microliters of sample arranged in an 8×12 matrix, for example, and thereby can be capable of holding many samples. A sample can contain, for example, a large number of nucleic acids having a suitable length or size, and can be labeled with fluorescent dyes, or the like, for identifying the 4 types of nucleotide base molecules. For the sample injection, the load header 113 and the sample container 124 can be arranged so that individual injecting end portions 120 are situated in individual sample vessels. While each injecting end portion 120 is immersed in a sample, electrophoresis can be carried out to introduce the sample into the capillaries 101.

According to various embodiments, a buffer container can be a container for containing the buffer into which the injecting end portions 120 are immersed when electrophoresis is carried out.

According to various embodiments, a separation medium replenishment system can include a block 104 and a syringe 110, and the system can fill the capillaries 101 with a separation medium, such as a polymer solution. The block 104 can be connected to the capillary head 105 and the syringe 110, and a part of the block 104 can be brought into contact with a buffer 116. When the separation medium is replenished, a valve 106 can isolate the syringe 110 from the buffer 116. The separation medium in the syringe 110 can be pumped into the capillaries 101 from the filling end portions via the capillary head 105 with high pressure. During electrophoresis, the valve 106 can be opened to communicate the filling end portions of the capillaries 101 with the buffer 116, to form a part of the current-carrying path.

According to various embodiments, an optical system can include a fluorescence excitation system that can illuminate the detection cell 108 with excitation light, and a light detection system that can detect light emitted from the detection cell 108.

According to various embodiments, the fluorescence excitation system can include a laser light source 114, a mirror, a beam splitter, and a condensing lens. Laser light 109 emitted from the laser light source 114 can be divided into two beams by the beam splitter, and their irradiation directions can be adjusted with the mirror and the condensing lens. This can enable the two substantially coaxial beams of laser light 109 each having different traveling directions, to illuminate the detection cell 108 on more than one side of the detection cell 108. The laser light 109 can be focused by the lens-like function of the capillaries 101 and can be transmitted through all of the capillaries 101. The laser light 109 can illuminate portions of the capillaries 101 in a periodically-timed manner according to various embodiments.

According to various embodiments, the detection optical system can include a detection lens, a CCD camera, and a computer, and can detect light emitted from the detection cell 108. The fluorescence emitted from each light illumination portion of the capillaries 101 can be transmitted through a detection lens located adjacent to the detection cell 108. It can be dispersed by wavelength using a grating or prism and can be detected with the CCD camera. A signal from the CCD camera can be processed by a computer to analyze the sample.

According to various embodiments, a power source system 112 can apply a high voltage to a current-carrying path extending at least from the injecting end portions 120 of the capillaries 101 to the detection cell 108. The current-carrying path can include the hollow electrodes 102, a buffer, capillaries 101, a separation medium in the block 104, a buffer 116, and a ground electrode 107. The high voltage power source 112 can apply a high voltage of about 15 kV to the current-carrying path, with the hollow electrodes 102 and the ground electrode 107 arranged as negative and positive potentials, respectively. This can cause an electric field in the direction from the detection cell 108 toward the injecting end portions 120, and therefore, negatively charged nucleic acids, and the like, can migrate in the direction from the injecting end portions 120 to the detection cell 108. At the time of sample injection, the buffer solution is replaced with a sample in the sample container 124. According to various embodiments, a pulse voltage can be applied to the current-carrying path.

According to various embodiments, the thermostatic oven 111 can be a temperature control apparatus for keeping the temperature of the individual capillaries 101 constant. The thermostatic oven 111 can accommodate a large portion of the capillaries 111, from the injecting end portions 120 to the detection cell 108, and can keep them at a constant temperature with temperature-controlled air flow. This can reduce differences in sample migration speeds attributable to temperature differences between individual capillaries 101.

Sample analysis by the electrophoresis device is described herein. According to various embodiments, when a high pulse voltage is applied to the current-carrying path, while the injecting end portions 120 are immersed in the sample 103, the sample 103 can be injected into the capillaries 101. The injecting end portions 120 can be immersed in a buffer and a high voltage can be applied to the current-carrying path to conduct electrophoresis. When sample components having different sizes pass through the separation medium inside the capillaries 101, they move faster when resistance is smaller. This enables smaller samples, which move more easily through the separation medium to reach the detection cell 108 faster as compared to larger components. The samples can then be illuminated with laser light 109 at the light illumination portions of the capillaries 101 to produce emitted light. The emitted light can be detected and analyzed in accordance with characteristics such as size of the sample emitting the light.

Figure 2:
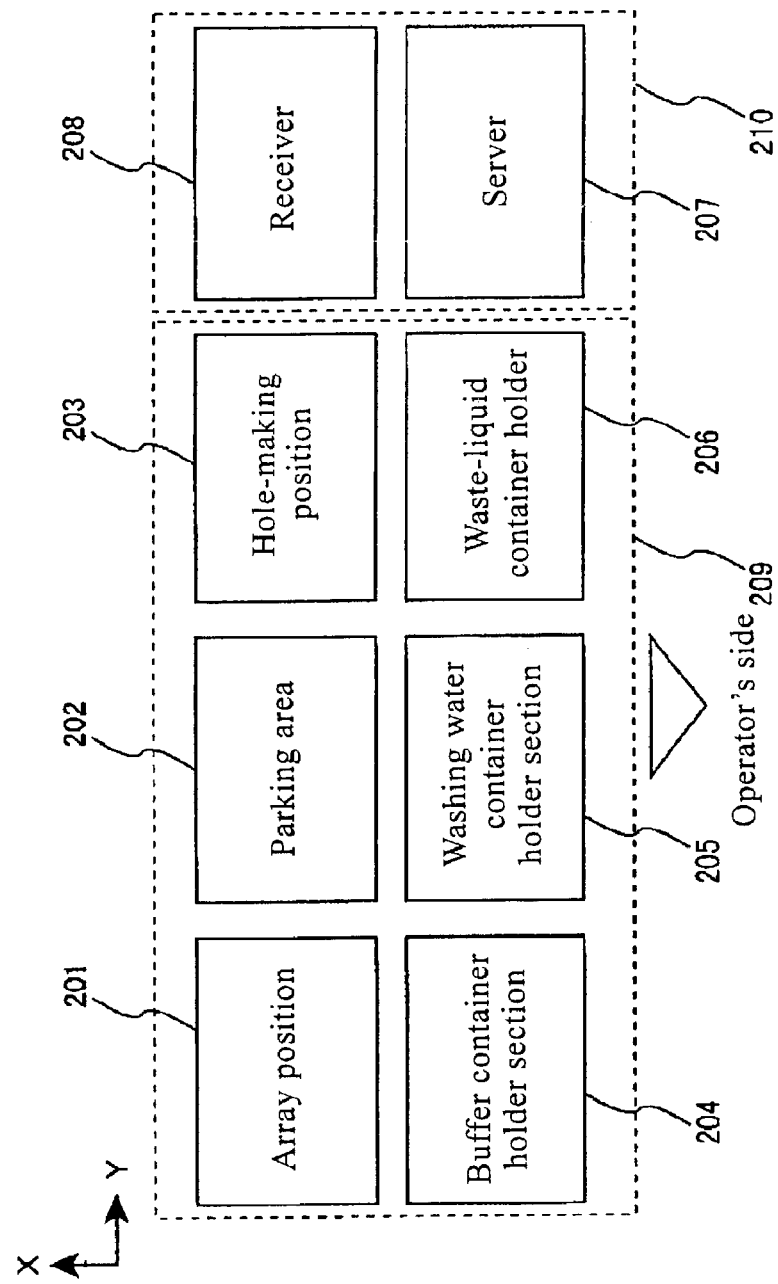
FIG. 2 is a schematic top view of a station and a stacker according to various embodiments.
Figure 3:
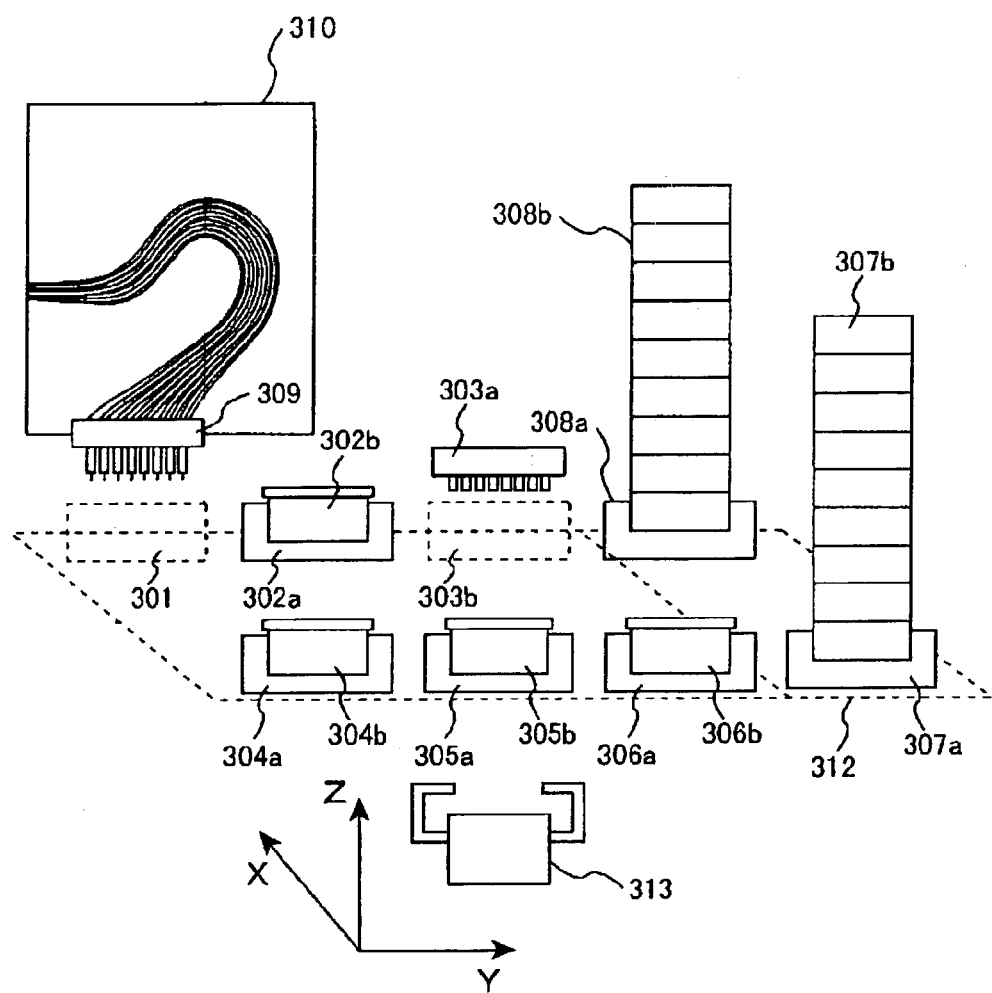
FIG. 3 is a schematic view of the station, the stacker, and a gripper according to various embodiments.

FIG. 2 is a schematic view of a layout of an autosampler. FIG. 3 is a schematic view in the vicinity of the autosampler. With reference to FIGS. 2 and 3, the autosampler will be described hereinafter.

According to various embodiments, the autosampler is an apparatus that can transport a container containing solutions for an electrophoresis assay, such as a sample container. The autosampler can make holes in a protection film covering the sample container, as will be described below. The autosampler can read barcodes attached to the sample container. The autosampler can include two regions, a station 209 and a stacker 210.

According to various embodiments, the station 209 can have 6 areas that can be divided into two rows, front and back, relative to a position of an operator. At the front or operator's side, a buffer container holder section 204, a washing water container holder section 205, and a waste-liquid holder 206, can be provided starting from the left side and moving right. At the back side, an array position 201, a parking area 202, and a hole-making position 203 can be provided starting from the left side and moving right. The apparatus can improve convenience by locating the buffer container, or other components that can be handled by the operator, at the front side. By arranging areas that the operator usually does not need to handle at the back side of the station, erroneous actions attributable to the operator can be minimized. For example, the parking area 202 (302a in FIG. 3), that can temporarily hold the sample container, can be provided at the back side. This allows carrying out the operation of taking in and out the sample container only through the stacker 210, and prevents the operator from performing this operation directly through the parking area 202.

According to various embodiments, the buffer container holder section 204 can be an area for detachably holding the buffer container. The buffer container can be used most frequently during the electrophoresis separation assay, and thus, can be placed near the array position. The buffer container can be full of a buffer into which the hollow electrodes 102 and injecting end portions 120 of the capillaries 101 are immersed during electrophoresis. Further, the separation medium inside the injecting end portions 120 can be prevented from drying by immersing the injecting end portions 120 in the buffer while the apparatus is in a standby mode.

According to various embodiments, the washing water container holder section 205 (305a in FIG. 3) can be an area for detachably holding the washing water container 305b. The washing water container 305b can contain water for washing used separation medium remaining after separation medium exchange, sample solution adhering thereto after sample injection, or the like, from the tips of the injecting end portions 120. After an injecting end portion 120 is immersed in a prescribed solution, it can be washed to prevent the contamination of the separation medium in the capillary and to remove excess material. As the washing water container can be less frequently used than the buffer container, it can be located further away from the array position 201 than the buffer container holder section 204.

According to various embodiments, the waste-liquid container holder 206 (306a in FIG. 3) can be an area for detachably holding the waste liquid container 306b. The waste-liquid container 306b can contain water and can store used separation medium discharged from the capillaries 101 during the separation medium exchange. As the waste-liquid container 306b is less frequently used compared to the washing water container 305b, it can be located further from the array position 201 than the washing water container holder section 205.

According to various embodiments, in the array position 201, electrodes of the capillary array can be arranged. A sample can be injected into an electrode end while the capillary is filled with the separation medium, and a further electric potential difference can be applied to both ends of the capillary to conduct electrophoresis.

According to various embodiments, the parking area 202 can be an area for detachably holding the sample container 302b. The gripper 313 can hold one container at a time, and thus the sample container can be held at the parking area 202 (302a in FIG. 3) while the gripper 313 holds other containers.

According to various embodiments, in the hole-making position 203, needles can be provided for making holes in a film. When a sample container is covered with a protection film for preventing liquid evaporation, the sample container can be moved so that the needles can penetrate the protection film to make holes, for the insertion of the hollow electrodes, and the injecting end portions 120.

According to various embodiments, the stacker 210 can be an area for storing sample containers before and after assay, and can be located at the right side of the station 209 to improve access for right-handed users that may account for a large portion of users.

According to various embodiments, a server 207 can be provided at the front side, and it can be a unit for storing sample containers that are to be subjected to assay. Sixteen sample containers can be stacked and stored. From the server 207, sample containers can be sequentially sent out for electrophoresis assay.

According to various embodiments, the receiver 208 can function to sequentially store sample containers whose samples have been assayed. Sixteen sample containers can be stacked and stored therein.

Figure 4:
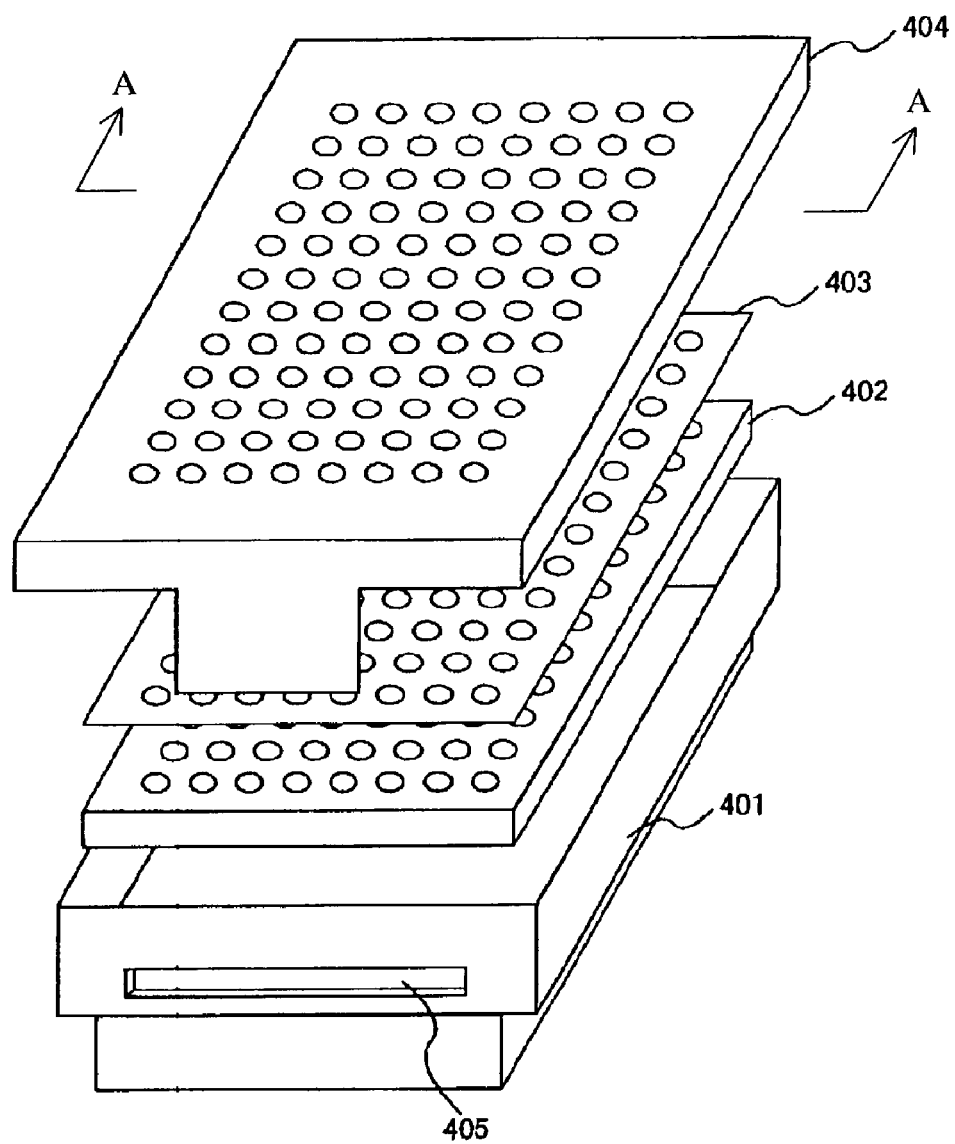
FIG. 4 is a perspective view illustrating members of a sample container according to various embodiments.
Figure 5:
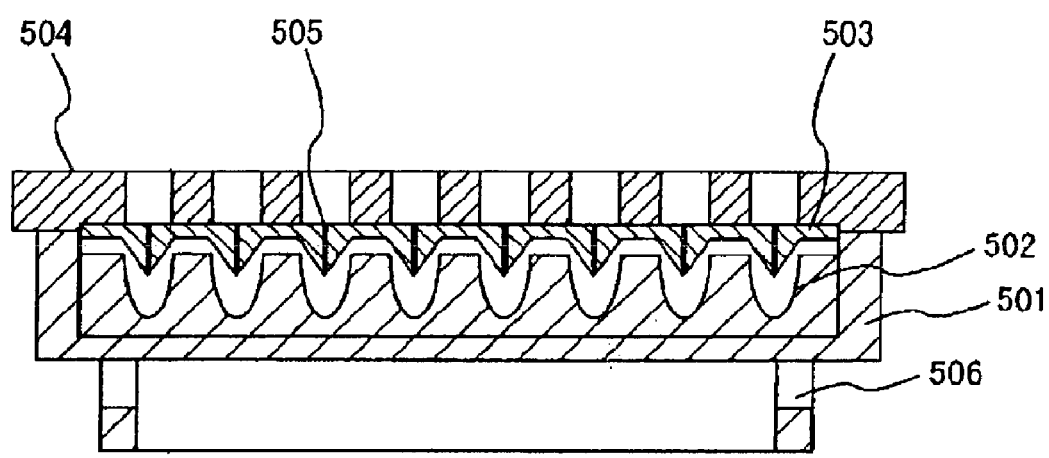
FIG. 5 is a cross-sectional view of the sample container according to various embodiments.

FIG. 4 is a schematic view of a sample container, and illustrates the individual members making-up the sample container after disassembly. FIG. 5 is a cross sectional view, taken along line A—A of FIG. 4, of the sample container. Hereinafter, the sample container will be described with reference to FIGS. 4 and 5.

According to various embodiments, the sample container can be a component for holding a plurality of samples intended for assay by electrophoresis. The sample container can be composed of 4 parts: a holder 401 (501 in FIG. 5), a sample plate 402 (502 in FIG. 5), a septum 403 (503 in FIG. 5), and a clip 404 (504 in FIG. 5), that can be overlapped.

According to various embodiments, the holder 401 can be a basic part of the sample container. The sample plate 402 and the septum 403 can be sandwiched between the holder 401 and the clip 404, and a hook of the clip 404 can be inserted into and engaged with an attachment groove 405 of the holder 401 to integrate each of the four parts. Further, the holder 401 can have a connection hole 506 for inserting a handle of the gripper 313 into to hold each container. The insertion of the handle into the connection hole 506 can enable a strong connection between the sample container and the gripper 313.

According to various embodiments, the sample plate 402 can have 96 or 384 wells (in an 8×12 matrix, or a 16×24 matrix), useable as pocket-type sample holders into which the sample solution can be inputted and held.

According to various embodiments, the septum 403 can be a resin sheet, and can have through-holes 505 for the insertion of the hollow electrodes at positions corresponding to individual wells. The through-holes 505 can be closed except when the hollow electrodes are inserted, to prevent sample solution in wells from evaporating. The through-holes 505 can function to allow the electrodes to enter by providing indentations. The evaporation of the sample solution can be prevented by attaching a protection film over a top surface of the septum 403 and/or the sample container.

Figure 6:
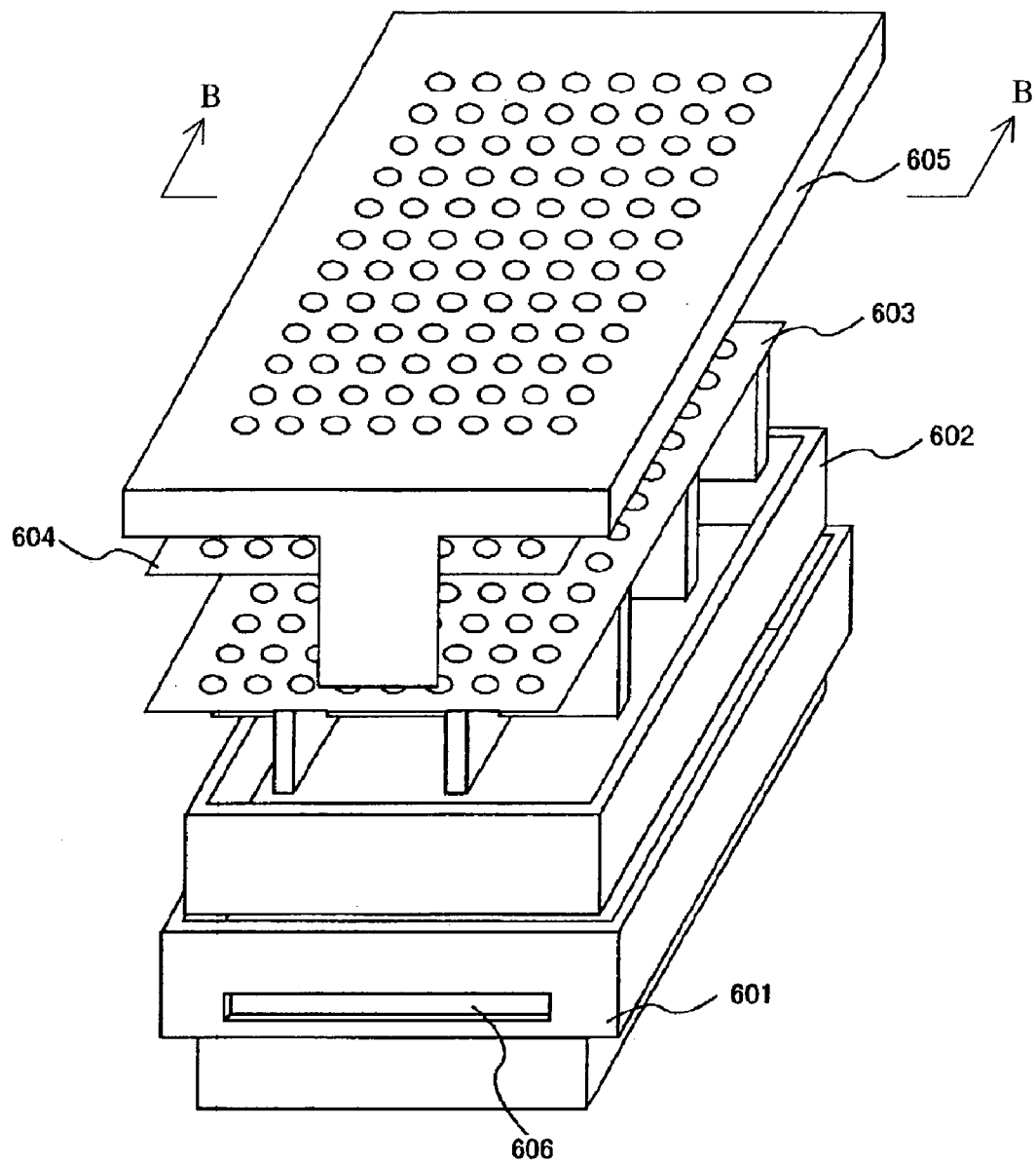
FIG. 6 is a perspective view showing members of a buffer container according to various embodiments, the buffer container having a configuration that is similar to a washing water container and a waste liquid container.

FIG. 6 is a schematic view of a container commonly used as the buffer container, the washing water container, and the waste-liquid container, and shows the members after disassembly.

Figure 7:
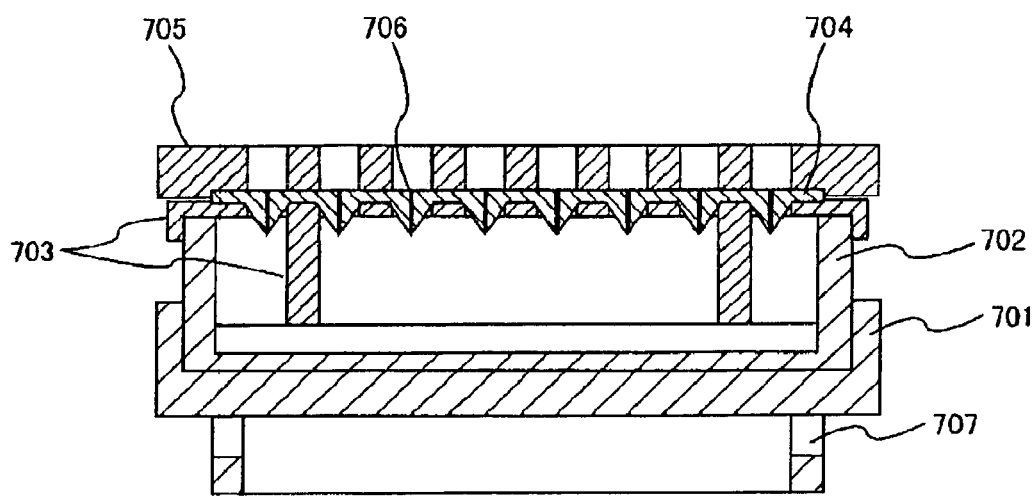
FIG. 7 is a cross-sectional view of the buffer container according to various embodiments.

FIG. 7 is a cross sectional view taken along line B—B of FIG. 6. The buffer container, the washing water container, and the waste-liquid container will be described by referring to these figures with a focus on the buffer container.

According to various embodiments, these containers can be composed of a holder 601 (701 in FIG. 7), an inner container 602 (702 in FIG. 7), a wave-dissipating plate 603 (703 in FIG. 7), and a clip 605 (705 in FIG. 7). A combination of the clip 605 and the holder 601 can be implemented, similar to the sample container, so that a hook of the clip 605 can be inserted into and engaged with an attachment groove 606 of the holder 601.

According to various embodiments, the holder 601 (701 in FIG. 7) can be a basic component of the container, and can have an external shape identical to the sample container holder, and further can have a connection hole 707 for inserting a handle of the gripper 313. Thus, it can be detachably held with the gripper 313 for transportation to a predetermined location.

According to various embodiments, the wave-dissipating plate 603 (703 in FIG. 7) can operate to restrict waves from forming in the solution held in the inner container and can support the septum 604 (704 in FIG. 7). The wave-dissipating 603 plate can be provided with wall-like members in a grid manner to divide the inside of the container into 12 areas (arranged in a 3×4 matrix). The surface of the fluid held in the container can be divided into small areas, whereby the occurrence of waves can be substantially prevented during transport of the container. As the divided area becomes smaller, the effect of wave dissipation can be enhanced. However, when the divided area is smaller than about the size of a finger, it may not be suitable for washing. Therefore, areas around the center of the container have a size of about 35 mm by about 35 mm, areas at the peripheral parts can have a size of about 35 mm by about 16 mm, and areas at the corner parts can have a size of about 16 mm by about 16 mm. Further, the wave-dissipating plate 603 does not necessarily extend to the bottom of the container, and the fluid can move from one divided area to another divided area, and thus the height of the surface of the fluid can be equal for all the divided areas. This can be desirable because all the hollow electrodes can be required to be immersed in the fluid at the same depth for washing and electrophoresis.

Assuming that the buffer container and washing water container are transported to the array position at a high speed, without the wave-dissipating plate, waves can be formed on the fluid surface at the end of container transportation, and it is not assured that all of the injecting end portions 120 would always be immersed in the fluid. The occurrence of waves can cause temporary exposure of the injecting end portions 120 to air. Such a condition is not desirable when applying a high voltage when performing electrophoresis. If each container is transported at a low speed so as not to cause waves in a solution, the injecting end portions 120 can be exposed to air over a long period. If the injecting end portions 120 are exposed to air for 14 seconds or more during the period from pre-electrophoresis to sample injection, their resolution can deteriorate. In addition, when waves exist on the surface of the fluid, it can be difficult or impossible to obtain the correct period of air-exposure for the injecting end portions 120.

If each container is transported at a high speed without the wave-dissipating plate, there is the possibility that the solution could be scattered outside the container. When the solution adheres to a structure situated around the capillaries, the application of high voltage during electrophoresis can cause a short circuit or an electric discharge, thereby resulting in erroneous operation or failure of the device. If buffer solution is scattered and adheres to the device, and then dries and becomes fixed thereto, its removal could be very difficult. Moreover, when the wave-dissipating effect is imparted to the container, the above problems can be avoided.

According to various embodiments, in addition to the wave-dissipating plate, there are other ways according to various embodiments, to provide a member resistant to the fluid, for example, by providing pits and projections at the container bottom surface, or by arranging stick members in a matrix arrangement.

According to various embodiments, there are additional ways to provide the container with a fluid-retaining member. For example, the container can be provided with a fluid-retaining member that is porous and flexible, like a sponge, and has excellent water-bearing properties. When the buffer and washing water are transported while they are soaked in such a member, the container can be transported at a high speed without scattering the solution outside of the container. The fluid-retaining member can be easily punctured by the insertion of the hollow electrodes, and can allow the injecting end portions 120 to be immersed in the fluid.

According to various embodiments, the waves on the surface of the fluid can be substantially eliminated, and the prevention of fluid scattering can be obtained, for example, by covering the fluid surface with a liquid phase coating that has a high viscosity and a low density. Instead of the liquid phase coating, a large number of floating members that are smaller than the intervals between individual injecting end portions may be arranged on the fluid surface.

According to various embodiments, the gripper 313 of FIG. 3 can be provided with an actuator that vibrates the container in the directions of the X, Y, and Z axes. A fluid speed detecting sensor can be provided that detects the direction and speed of the waves of the fluid in the container. Such a structure can provide movements to the container to reduce waves in the fluid.

Figure 8:
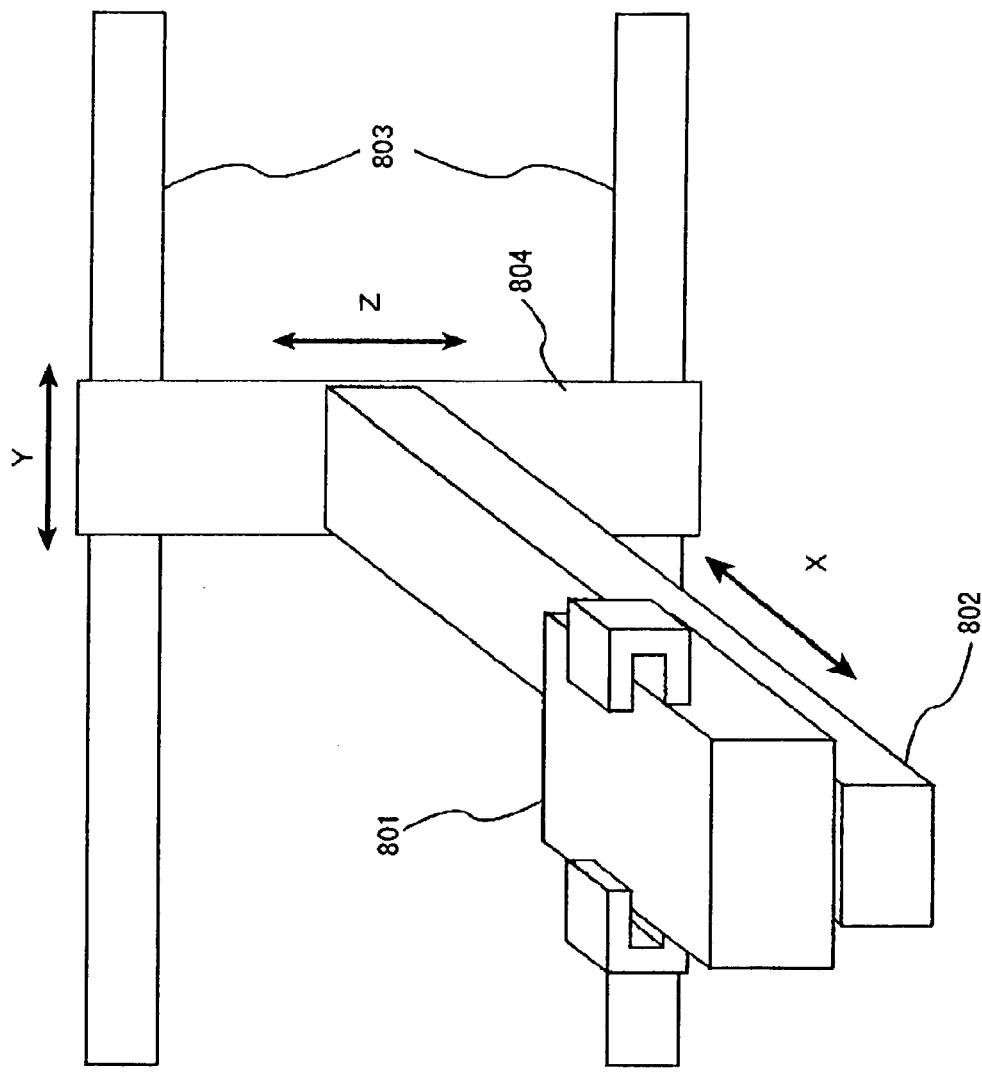
FIG. 8 is a schematic view of a gripper according to various embodiments.
Figure 9:
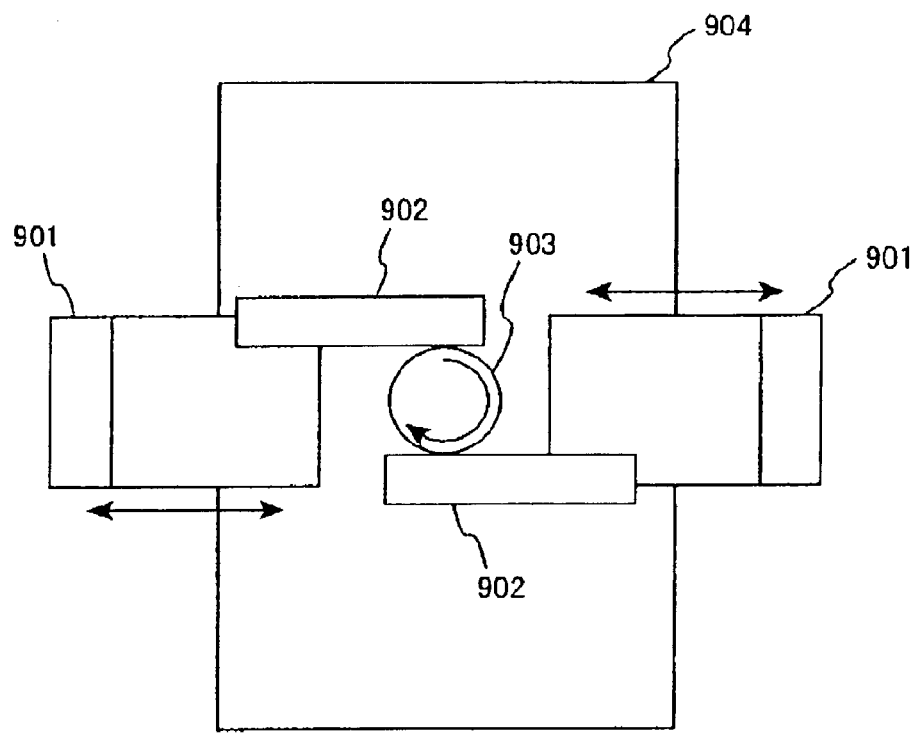
FIG. 9(a) is a schematic top view of a container holding function of the gripper according to various embodiments.
FIG. 9(b) is a schematic view of the gripper in a hold position according to various embodiments.
FIG. 9(c) is a schematic view of the gripper in a release position according to various embodiments.
Figure 9:
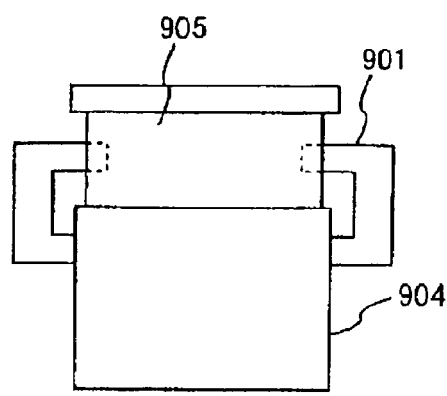
Figure 9:
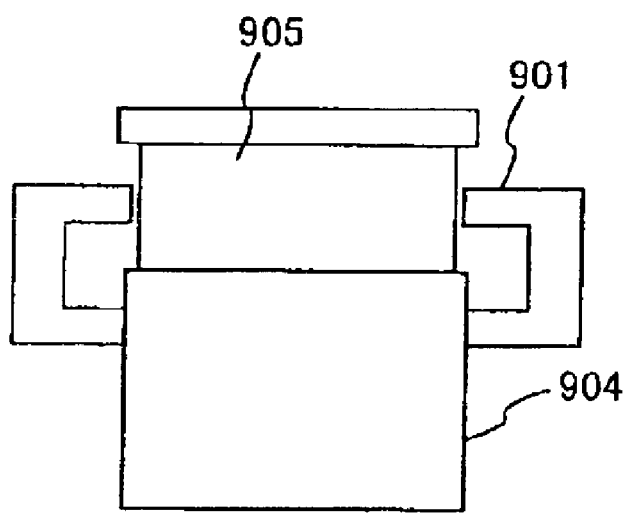

FIG. 8 is a schematic view of an autosampler that can transport the container. FIG. 9(a) is a schematic view that illustrates the internal mechanism of the gripper. FIG. 9(b) is a schematic view that illustrates the mechanism at the time of holding, and FIG. 9(c) is a schematic view that illustrates the mechanism at the time of releasing. Hereinafter, the gripper will be explained with reference to FIGS. 8, and 9(a) to 9(c).

According to various embodiments, the gripper 801 can be arranged to move on a linear guide 802 along with X-axis. Also, the linear guide 802 can be orthogonal to a linear guide 804 along a Z-axis, and the linear guide 804 can be orthogonal to a linear guide 803 along a Y-axis. The individual linear guides can be arranged to be orthogonal to each other. According to various embodiments, the gripper 801 can move on three axes, X, Y, and Z. As a result, the gripper 801 can be moved to any position along a three-dimensional coordinate system within the autosampler.

FIG. 9(a) shows a mechanism for attaching and detaching each container using the gripper 801. The container attaching and detaching mechanism of the gripper can be composed of handles 901, that can be inserted into connecting holes in the container, racks 902 that can be fixed to the handles, and a pinion 903 that can be connected to a motor to move the racks 902 and handles 901 back and forth by way of the motor's rotation. The direction of movement of the handles 901 can be controlled by switching the motor rotation between forward and reverse, and the movement can be controlled by the rotational amount. This can enable a changeover between a "hold" position where the container 905 can be held with the gripper and the "release" position, where the container can be released from the gripper.

Container transportation will be described using the example where a buffer container is transported from the buffer container holder section 204 to the array position 201.

According to various embodiments, the gripper 313 can move the buffer container holder section 204 when its handle is in the release condition, and thereafter, when the handle is in the hold condition, the buffer container can be fixed to the gripper 313. The gripper 313 can then move to the array position 201 and push the buffer container upwards to the hollow electrodes 102 to immerse the injecting end portions 120 in the buffer. In returning the buffer container to the buffer container holder section 204, the buffer container can be pulled down to release it from the load header. Then, the gripper 313 can move to the buffer container holder section 204, and can release its handles, thereby returning the container to the holder.

According to various embodiments, the gripper has a configuration that allows it to hold and release a single container. This can avoid increasing the area occupied by the gripper, increasing the weight of the gripper, increasing dead space in the autosampler, increasing the weight of the autosampler, all of which would occur in an attempt to transport a plurality of containers with the gripper at the same time. When transporting a plurality of containers at the same time with the gripper, the total weight and the occupied area of the autosampler would be increased as explained below. Assuming that a container having a size of L×T is transported within an area range of LL×TT, a space of (LL+2−L)×TT would be required when two containers aligned in an L direction are transported together. In other words, an autosampler would need to have an additional area of 2×L×TT in comparison with a situation where the autosampler transports only one container. Considering the prevention of deformation due to flexure of the device, size would need to be increased to maintain rigidity. Thus, weight increase becomes much larger than the area increase ratio, 2×L/LL. When the container area is larger, increases of dead space and weight become significant. When a large-capacity sample container having 96 wells or more is handled, it is difficult to perform micro control because of the weight increase.

Figure 10:
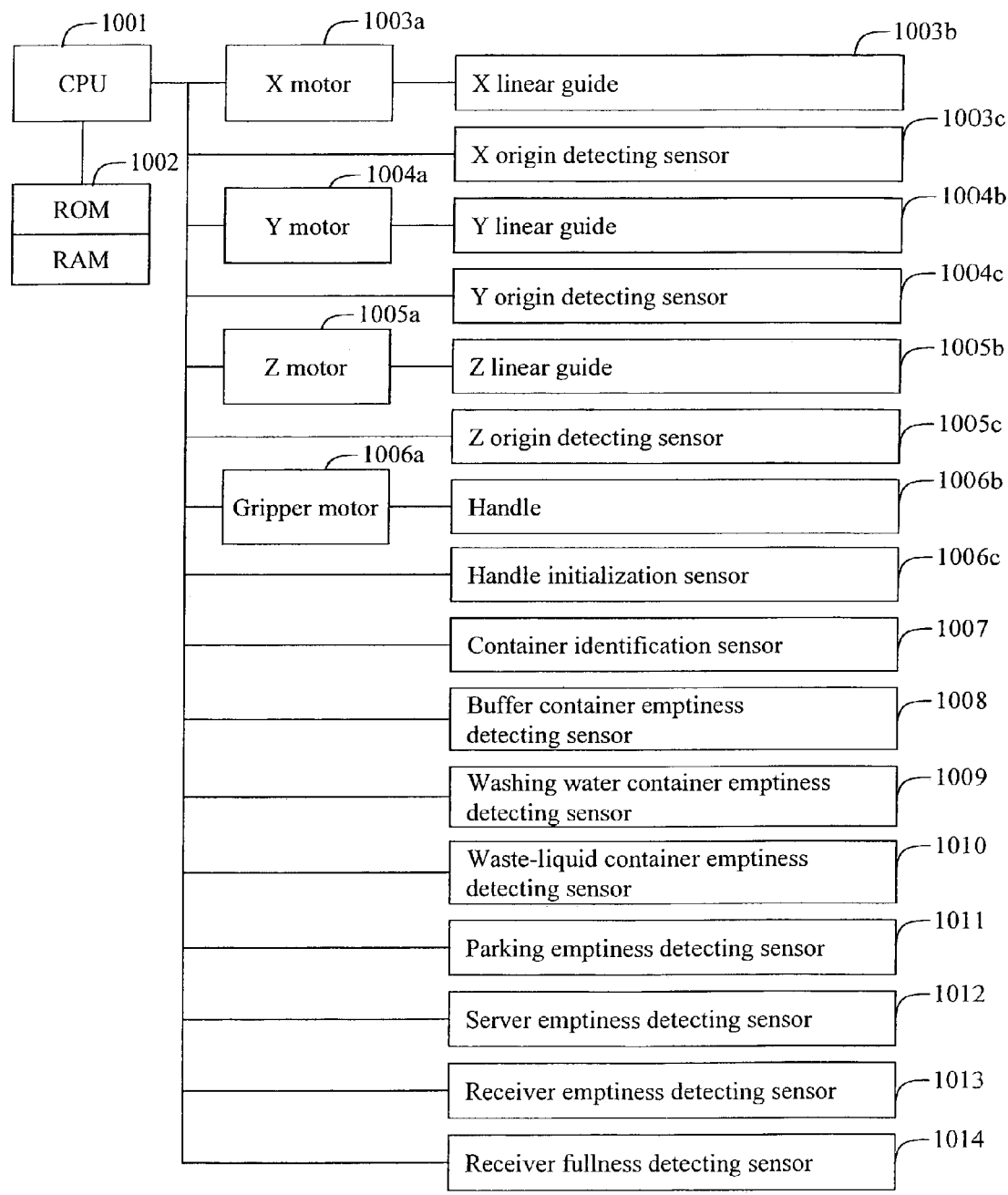
FIG. 10 is a control circuit diagram according to various embodiments.

FIG. 10 is a control circuit diagram for an autosampler-type mechanism. An autosampler control circuit will be described with reference to FIG. 10. The autosampler control circuit can have a basic configuration comprising: a CPU 1001; a memory 1002; an X-axis motor 1003a, a Y-axis motor 1004a, and a Z-axis motor 1005a that can all operate as actuators for transporting the gripper in the X, Y, and Z directions; and an X-axis linear guide 1003b, a Y-axis linear guide 1004b, and a Z-axis linear guide 1005c, that can all operate to convert the rotational movement of the motor to linear movement to transport the gripper to any coordinate position. In FIG. 10, the X-axis motor can be an actuator for transporting the gripper in the X-axis direction, and in a similar way, the Y-axis and Z-axis motors can be actuators for transporting the gripper in the Y and Z axes directions, respectively. Further, each linear guide, for the X, Y, or Z axes, has a function of converting the rotational movement of the motor to linear movement for transporting the gripper to any coordinate position.

According to various embodiments, when data in the memory 1002 corresponding to the present gripper position is lost as a result of turning-on, power failure, or the like, individual linear guides can be provided with X, Y, and Z origin detecting sensors for origin positioning.

In addition, the autosampler control circuit can be provided with a gripper motor 1006a for controlling the hold/release of the container by the gripper, a handle 1006b, and a handle initialization sensor 1006c for detecting a handle position at the time of initialization. On the upper surface of the gripper, a container identification sensor 1007 can be provided for identifying a type of container (buffer container or the like) held thereon. In combination with this structure, and with a buffer container emptiness detecting sensor 1008, a washing water container emptiness sensor 1009, a waste-liquid container emptiness detecting sensor 1010, and a parking emptiness detecting sensor 1011, a proper container can be transported to the array position, a container holder section, the parking area, and the like. The emptiness detecting sensors can be located on respective container holders and the parking area, and can detect whether respective containers are placed therein.

Also, a server emptiness detecting sensor 1012 can be provided that can detect whether sample containers remain which have not yet been subjected to assay. Further, an emptiness detecting sensor and a fullness detecting sensor can be provided to enable the determination whether or not the receiver has an assayed sample container, and if it has, whether or not the receiver's capacity is fully utilized with the maximum accommodation number of the containers. The emptiness detecting sensor and fullness detecting sensor can also determine whether the receiver lacks space for further containers. The emptiness detection and fullness detection can be carried out using reflection sensors, that can make determinations by detecting the reflection of light emitted toward a container.

Figure 11:
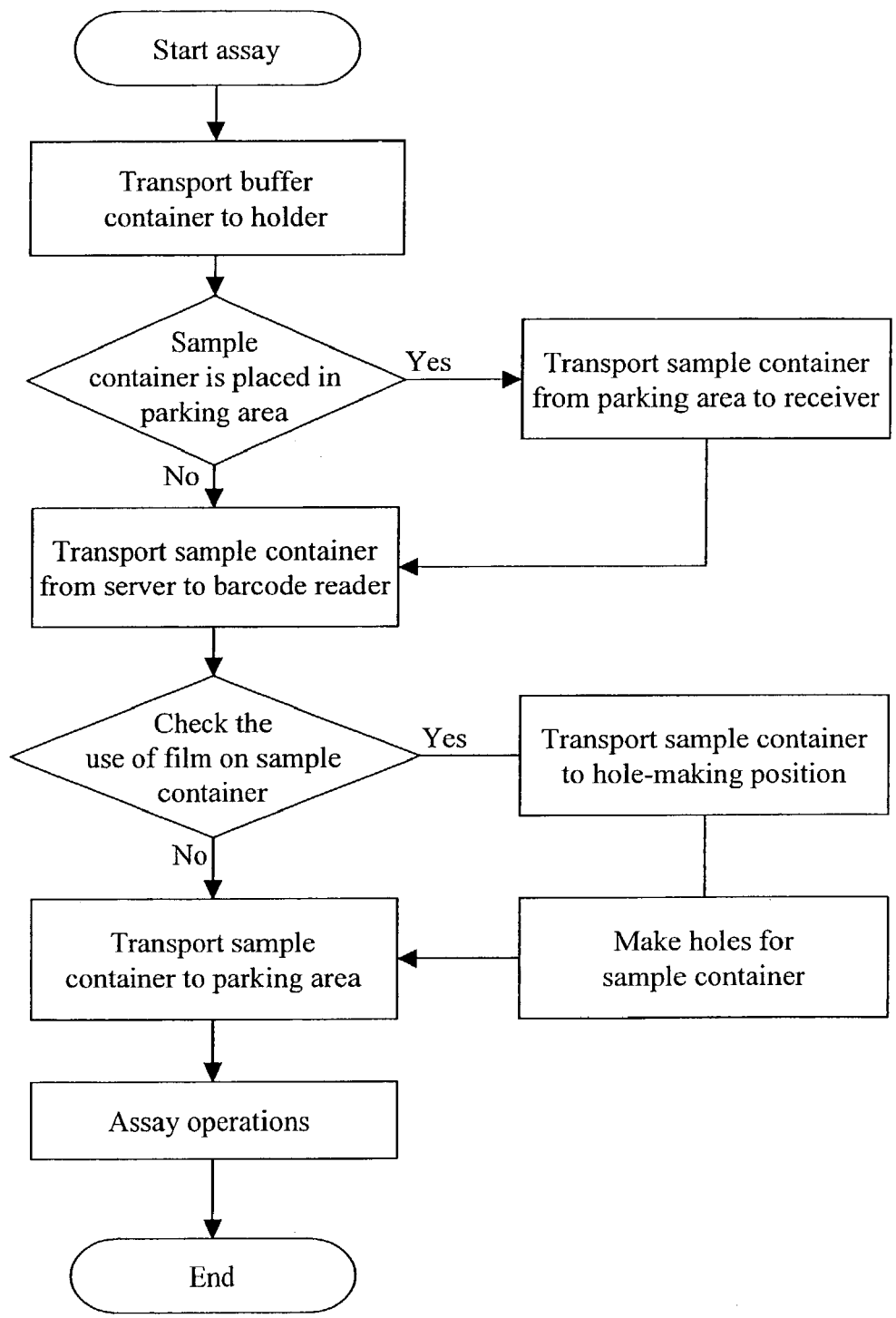
FIG. 11(a) is an assay flowchart according to various embodiments.
FIG. 11(b) is a list of assay operation procedures for the assay flow according to various embodiments.

FIG. 11(a) is a flowchart illustrating an entire standard assay operation. FIG. 11(b) is a list of operation modes illustrating assay operations in detail. Operation steps of the present device will be described with reference to FIGS. 11(*a*) and 11(*b*). In the assay operation flow chart, the autosampler with a barcode reader can be used to read a barcode attached to a sample container.

According to various embodiments, in a stand-by condition before assay-starting, the buffer container can be placed in the array position. This can prevent the separation medium of the electrode tip from drying by immersing the injecting end portion 120 in the buffer. As described below, when the separation medium in the capillary is dried and altered, such alteration tends to induce the deterioration of assay accuracy, such as a decline in resolution during electrophoresis.

According to various embodiments, when the assay operation starts, it can be confirmed that no sample containers are placed in the parking area. Then, a sample container can be brought out from the server and transported to a position where a barcode reader can read a barcode.

Subsequently, the barcode of the container can be read to allow the crosscheck after the assay between inputted sample data and data obtained through the assay.

Next, when the sample container is covered with a film for preventing sample evaporation, the sample container can be transported to a hole-making position to form holes in the film. After making the holes, or when the film for preventing sample evaporation is not used, the sample container can be placed in the parking area to conduct the assay operations.

The assay operations starting with the separation medium filling operation of the capillary, will be described based on FIG. 11(*b*). FIG. 11(*b*) indicates operations to be performed, and, when the operation is container transportation, containers intended for transportation and containers' positions before and after transportation.

First, the waste-liquid container can be transported to the capillary position, and placed so that the injecting end portion 120 can be immersed in the waste liquid (1). Next, as shown in FIG. 1, pressure can be applied to the separation medium in the syringe 110 to fill the capillaries 101 with the separation medium (2). The waste-liquid container can be placed under the capillaries to collect used separation medium that is pushed out from the syringe by newly filled separation medium. After separation medium filling, the waste-liquid container can be transported and placed in the holder (3). Then, the washing water container can be transported from the washing water container holder section to the capillary position and the hollow electrodes can be inserted into the washing solution. As a result, used separation medium attached to the outside of the electrodes can be removed (4). The washing water container can be transported and placed to the holder and the buffer container can be transported to the capillary position (5) (6). Next, while the hollow electrodes are immersed in the buffer, a high voltage can be applied between the hollow electrodes and a ground electrode 107 to conduct pre-electrophoresis (8).

Pre-electrophoresis is an operation that can stabilize properties of the separation medium during electrophoresis by applying a current to the separation medium in the capillaries having no samples contained therein. After pre-electrophoresis, the buffer container can be transported and placed in the holder, and the washing water container can be transported from its holder to the capillary position for washing the array (9) (10) (11). The container transportation between the pre-electrophoresis and the array washing should be completed within 14 seconds or less, and preferably within 10 seconds or less. This is because when the injecting end portions 120 are exposed to air for a long period, the separation medium at the tips of the capillaries can become dry and altered, thereby adversely affecting electrophoresis properties.

After the array washing, the washing water container can be transported and placed in the holder, and the sample container can be transported from the parking area to the capillary position (12) (13). The sample container transportation to the capillary position after the array washing should be completed within 14 seconds or less, and preferably within 10 seconds or less, for the reasons as discussed above. While the injecting end portions 120 are immersed in the samples, a pulsed voltage can be applied between the ground electrode and the hollow electrodes to inject the samples into the separation medium (14). After sample injection, the sample container can be transported and placed in the parking area (15). Thereafter, the washing water container can be transported from the holder to the capillary position for washing the array (16) (17). This array washing can remove samples adhering to the hollow electrodes and the outside of the capillaries so as to avoid the contamination of the buffer during electrophoresis. Thereafter, the washing water container can be transported and placed in the holder, and the buffer container can be transported from the holder to the capillary position (18) (19). While the injecting end portions 120 are immersed in the buffer, a high voltage can be applied between the ground electrode and the hollow electrodes to conduct electrophoresis (20). After the electrophoresis is completed, the buffer container can be transported and placed in the holder (21). The sample container can be transported from the parking area to the receiver and stored therein (22). Further, the buffer container can be transported from the holder to the capillary position, so that the injecting end portions 120 are immersed in the buffer. Then, a series of assay operations can be completed and the device can be placed in standby mode while the injecting end portions 120 are immersed in the buffer (23).

As described above, during the operations from (8), pre-electrophoresis, to (14), sample injection, the period of air exposure can be controlled, and can be shortened, to prevent the injecting end portions 120 from drying. Thus, when a separation medium that is sensitive to dryness is used, the exposure period can be 14 seconds, and preferably, 10 seconds or less. Because it is difficult to make the transportation distance shorter than the fixed distance due to the size of each container, shortening the exposure period by speeding up the transportation is desirable. Speeding up transportation can contribute to improvement of throughput in the assay operations.

Figure 12:
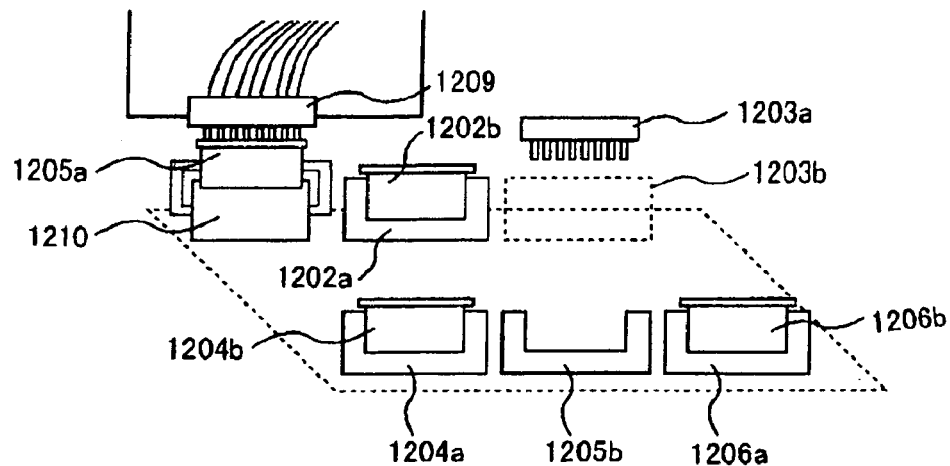
FIG. 12(a) is a schematic diagram showing an assay flow (array washing) according to various embodiments.
FIG. 12(b) is a schematic diagram showing an assay flow (storing a washing water container) according to various embodiments.
FIG. 12(c) is a schematic diagram showing an assay flow (holding a sample container) according to various embodiments.
FIG. 12(d) is a schematic diagram showing an assay flow (sample injection) according to various embodiments.
Figure 12:
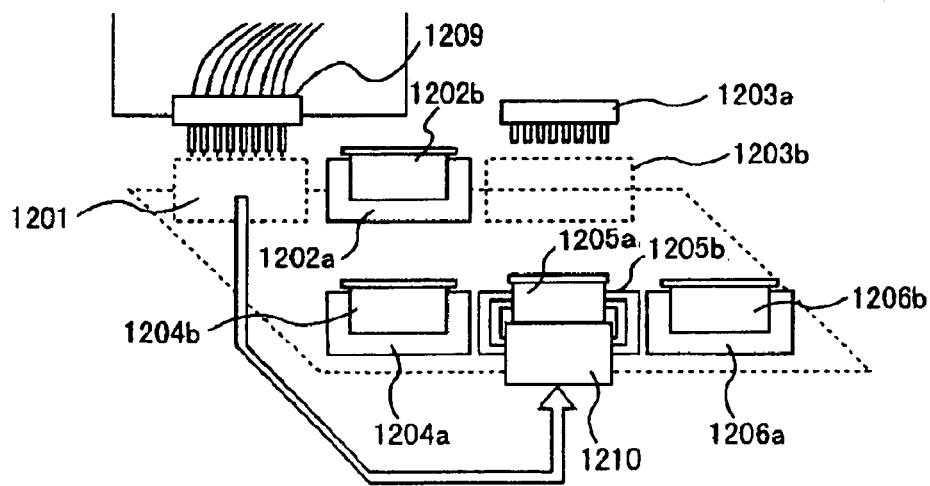
Figure 12:
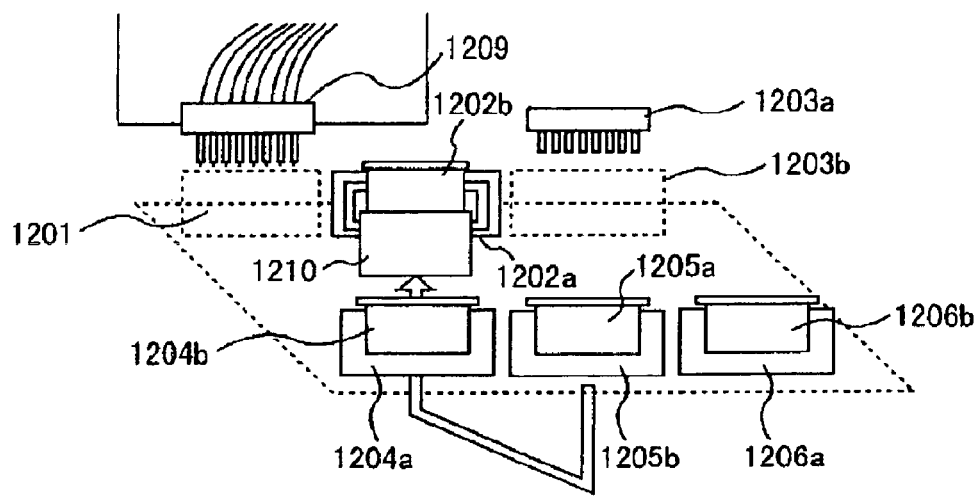
Figure 12:
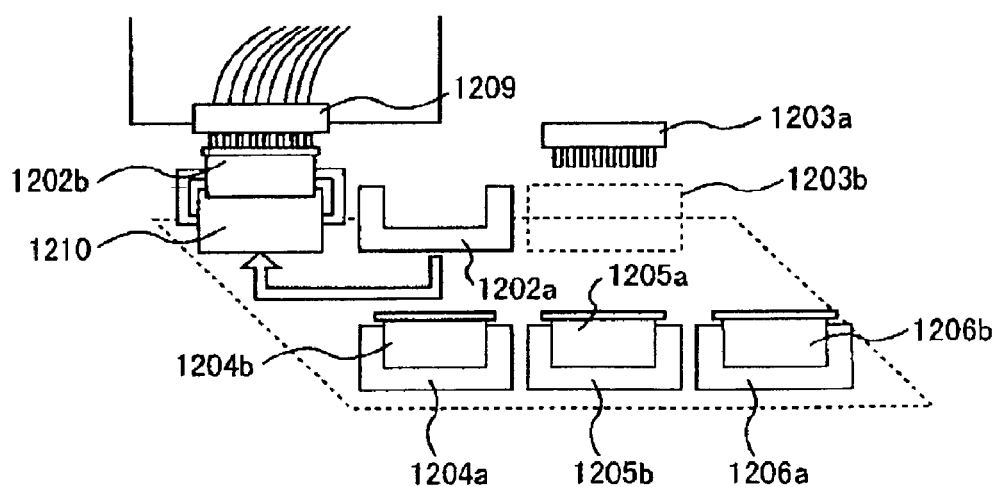

FIGS. 12(*a*) to 12(*d*) visually show individual operations from (11), array washing, to (14), sample injection.

First, after washing the array, the washing water container 1205*a* can be transported from the array position to the washing water container holder section 1205*b*.

According to various embodiments, after the gripper 1210 that holds the washing water container passes through the pathway indicated by an arrow, and moves to the washing water container holder section, it can release the container (FIG. 12(*b*)). Thereafter, the gripper can move to the parking area to hold the sample container 1202*b* (FIG. 12(*c*)). The gripper can move to the array position for sample injection (FIG. 12(*d*)). During this period, the gripper can repeat the movements in the directions of the X, Y, or Z-axes, as shown in figures. Therefore, when the gripper attempts to perform the operations described in FIGS. 12(*a*) to 12(*d*) within 14 seconds or less, and in particular within 10 seconds or less, the acceleration/deceleration of the gripper from side to side and up and down can become high. However, since the inside of the container can be divided and shielded into small areas by the wave-dissipating plate, waves in the fluid in the container can-be reduced even if the container is transported at a high speed. Thus, the injecting end portions 120 of the capillaries can be reliably inserted into the fluid within the time limit. Further, during container transportation, the buffer can be prevented from scattering outside the container. Since a high voltage can be applied to the device during electrophoresis, there is the possibility that scattered buffer may cause failures of the device due to a short circuit, an electric discharge, or the like. Furthermore, when the scattered buffer adhering to the device is dried, it is difficult to remove it. However, these problems do not arise when using the device according to various embodiments.

Figure 13:
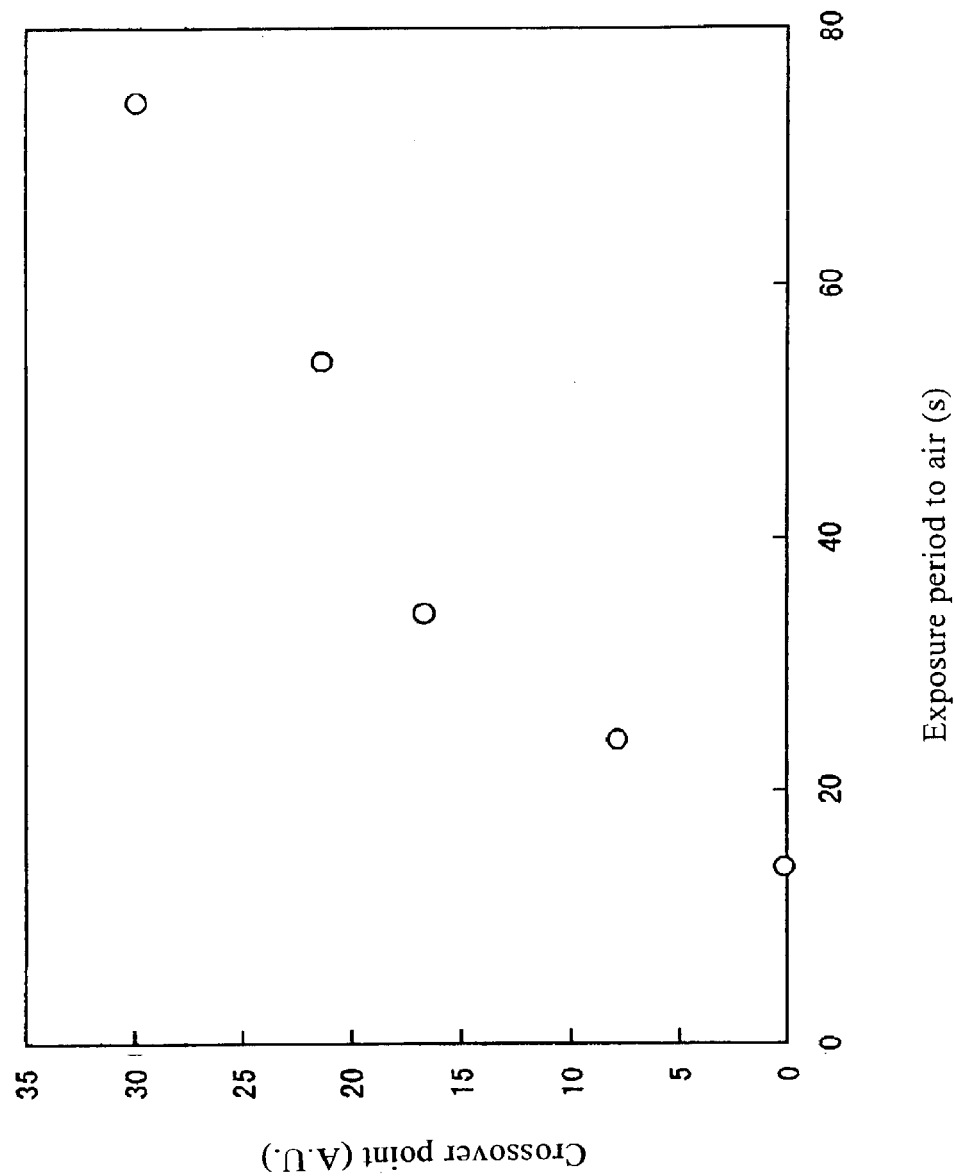
FIG. 13 is a graph showing the relationship between the period of air exposure of an injecting end portion and the crossover point according to various embodiments.

FIG. 13 is a graph illustrating the correlation between the air exposure period of the injecting end portion and the crossover points of assay results. The crossover point indicates the resolution of the device, and as its value becomes larger the resolution deteriorates. The exposure period is the period from array washing to sample injection. The period can be calculated from the time when all the injecting end portions 120 are pulled away from the washing water to the time when all the injecting end portions 120 make contact with samples. The separation medium that can be used for the assay is POP-7 gel available from Applied Biosystems. According to the assay results, such a polymer solution can be relatively sensitive to air exposure, and as a result, the crossover point can drastically deteriorate when the exposure period is greater than 14 seconds. However, the margin of the exposure period according to the various embodiments can be 10 seconds or less, so the separation medium can be used in excellent conditions.

According to the present invention, the resolution does not deteriorate during electrophoresis of samples. Further, sample throughput can be improved.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. An electrophoresis device comprising:
   a plurality of capillaries each being filled with a separation medium for sample separation, each capillary having an injecting end portion for introducing a sample and a light illumination portion capable of being illuminated with an excitation light;
   a power source device capable of applying a voltage to a current-carrying path extending at least between the injecting end portion and the light illumination portion of each of the plurality of capillaries;
   a fluorescence excitation device capable of illuminating the light illumination portion of each of the plurality of capillaries with light;
   a light detection device capable of detecting light emitted from the light illumination portion of each of the plurality of capillaries;
   a fluid container capable of holding a fluid into which the injecting end portions of each of the plurality of capillaries are immersed, the fluid container being provided with a fluid resistance member; and
   a container transportation device capable of transporting the fluid container;
   wherein, when a fluid is present in the fluid container, the fluid resistance member equalizes a height of the surface of the fluid, having contact with the injecting end portions of the plurality of capillaries.

2. The electrophoresis device of claim 1, wherein the fluid resistance member is a partition that is capable of dividing a surface of the fluid into a plurality of areas, when a fluid is present in the fluid container.

3. The electrophoresis device of claim 1, wherein the fluid resistance member is a member floating in the fluid.

4. The electrophoresis device of claim 1, wherein the fluid resistance member is a float floating in the fluid.

5. The electrophoresis device of claim 1, wherein the fluid resistance member is a sponge.

6. The electrophoresis device of claim 1, wherein the fluid container comprises a bottom and the fluid resistance member does not extend to the bottom.

7. An electrophoresis device comprising:
   a plurality of capillaries each being filled with a separation medium for sample separation, each capillary having an injecting end portion for introducing a sample and a light illumination portion capable of being illuminated with an excitation light;
   a power source device capable of applying a voltage to a current-carrying path extending at least between the injecting end portion and the light illumination portion of each of the plurality of capillaries;
   a fluorescence excitation device capable of illuminating the light illumination portion of each of the plurality of capillaries with light;
   a light detection device capable of detecting light emitted from the light illumination portion of each of the plurality of capillaries;
   a sample container capable of holding a plurality of samples, the sample container having a sample container usage position in which the samples held in the sample container are brought into contact with the injecting end portions of the plurality of capillaries;
   a fluid container capable of holding a fluid into which the injecting end portions of the plurality of capillaries are immersed, the fluid container being provided with a fluid resistance member;
   a sample container storage device capable of storing the sample container; and
   a transportation device capable of transporting the sample container from the sample container storage device to the sample container usage position within 14 seconds after the injecting end portion of each of the plurality of capillaries is exposed to air;
   wherein the fluid resistance member equalizes a height of the surface of the fluid having contact with the injecting end portions of the plurality of capillaries, when a fluid is present in the fluid container.

8. The electrophoresis device of claim 7, wherein the transportation device is capable of transporting the sample container from the sample container storage device to the sample container usage position within 10 seconds after the injecting end portion of each of the plurality of capillaries is exposed to air.

9. The electrophoresis device of to claim 7, further comprising a buffer container capable of holding a buffer for immersing the injecting end portion of each of the plurality of capillaries therein; wherein the transportation device capable of transporting the fluid container to a position in which the fluid is brought into contact with the injecting end portion of each of the plurality of capillaries within 14 seconds after each of the injecting end portions are separated from the buffer.

10. The electrophoresis device according to claim 9, wherein the transportation device is capable of transporting the sample container from the sample container storage device to the sample container usage position within 10 seconds after the injecting end portion of each of the plurality of capillaries is exposed to air, and is capable of transporting the fluid container to a position in which the fluid is brought into contact with the injecting end portion of each of the plurality of capillaries within 10 seconds after the injecting end portions are separated from the buffer.

11. The electrophoresis device according to claim 7, wherein the transportation device has a grip for detachably holding at least the sample container and the fluid container.

12. An electrophoresis device comprising:
a plurality of capillaries each capable of being filled with a separation medium for sample separation, each capillary including an injecting end portion for introducing a sample and a light illumination portion capable of being illuminated with an excitation light;
a power source device capable of applying a voltage to a current-carrying path extending at least between the injecting end portion and the light illumination portion of each of the plurality of capillaries;
a fluorescence excitation device capable of illuminating the light illumination portion of each of the plurality of capillaries with light;
a light detection device capable of detecting light emitted from the light illumination portion of each of the plurality of capillaries;
a fluid container capable of holding a fluid into which the injecting end portions of the plurality of capillaries are immersed, the fluid container being provided with a fluid resistance member; and
a container transportation device capable of transporting the fluid container;
wherein the fluid resistance member equalizes a height of a, surface of the fluid, having contact with the injecting end portions of the plurality of capillaries.

13. The electrophoresis device of claim 12, wherein the fluid resistance member is a partition that is capable of dividing a surface of the fluid into a plurality of areas.

14. The electrophoresis device of claim 12, wherein the fluid resistance member is a member floating in the fluid.

15. The electrophoresis device of claim 12, wherein the fluid resistance member is a float floating in the fluid.

16. The electrophoresis device of claim 12, wherein the fluid resistance member is a sponge.

17. The electrophoresis device of claim 12, wherein the fluid container comprises a bottom and the fluid resistance member does not extend to the bottom.

18. An electrophoresis device comprising:
a plurality of capillaries each capable of being filled with a separation medium for sample separation, each capillary including an injecting end portion for introducing a sample and a light illumination portion capable of being illuminated with an excitation light;
a power source device capable of applying a voltage to a current-carrying path extending at least between the injecting end portion and the light illumination portion of each of the plurality of capillaries;
a fluorescence excitation device capable of illuminating the light illumination portion of each of the plurality of capillaries with light;
a light detection device capable of detecting light emitted from the light illumination portion of each of the plurality of capillaries;
a sample container capable of holding a plurality of samples, the sample container including a sample container usage position in which the samples held in the sample container are brought into contact with the injecting end portions of the plurality of capillaries;
a fluid container capable of holding a fluid into which the injecting end portions of the plurality of capillaries are immersed, the fluid container being provided with a fluid resistance member;
a sample container storage device capable of storing the sample container; and
a transportation device capable of transporting the sample container from the sample container storage device to the sample container usage position within 14 seconds after the injecting end portion of each of the plurality of capillaries is exposed to air;
wherein, when a fluid is present in the fluid container, the fluid resistance member equalizes a height of a surface of the fluid, having contact with the injecting end portions of the plurality of capillaries.

19. The electrophoresis device of claim 18, wherein the transportation device is capable of transporting the sample container from the sample container storage device to the sample container usage position within 10 seconds after the injecting end portion of each of the plurality of capillaries is exposed to air.

20. The electrophoresis device of to claim 18, further comprising a buffer container capable of holding a buffer for immersing the injecting end portion of each of the plurality of capillaries therein; wherein the transportation device is capable of transporting the fluid container to a position in which the fluid is brought into contact with the injecting end portion of each of the plurality of capillaries within 14 seconds after each of the injecting end portions are separated from the buffer.

21. The electrophoresis device according to claim 20, wherein the transportation device is capable of transporting the sample container from the sample container storage device to the sample container usage position within 10 seconds after the injecting end portion of each of the plurality of capillaries is exposed to air, and is capable of transporting the fluid container to a position in which the fluid is brought into contact with the injecting end portion of each of the plurality of capillaries within 10 seconds after the injecting end portions are separated from the buffer.

22. The electrophoresis device according to claim 18, wherein the transportation device has a grip for detachably holding at least the sample container and the fluid container.

* * * * *